United States Patent [19]

Franklin

[11] Patent Number: 4,661,648
[45] Date of Patent: Apr. 28, 1987

[54] PROCESS FOR CARRYING OUT SUBSTITUTION CHLORINATION REACTIONS OF ORGANIC COMPOUNDS BY MEANS OF MOLECULAR CHLORINE IN THE PRESENCE OF A CHLORINATED PRODUCT SERVING AS A RADICAL INITIATOR, AND RADICAL INITIATORS USED IN SUCH A PROCESS

[75] Inventor: James Franklin, Brussels, Belgium

[73] Assignee: Solvay & Cie (Societe Anonyme), Brussels, Belgium

[21] Appl. No.: 765,965

[22] Filed: Aug. 15, 1985

[30] Foreign Application Priority Data

Aug. 20, 1984 [FR] France ................................ 84 13051

[51] Int. Cl.$^4$ ............................................ C07C 17/10
[52] U.S. Cl. ..................................... 570/208; 570/253; 570/198; 570/181; 570/189
[58] Field of Search ......................... 570/208, 253, 198

[56] References Cited

U.S. PATENT DOCUMENTS 2,299,441  10/1942  Vaughan et al. ................... 570/253

FOREIGN PATENT DOCUMENTS 2111671  9/1972  France ................................ 570/253
2190783  1/1974  France ................................ 570/253

Primary Examiner—Charles F. Warren
Assistant Examiner—Joseph A. Boska
Attorney, Agent, or Firm—Spencer & Frank

[57] ABSTRACT

The substitution chlorination reactions of organic compounds are carried out by means of molecular chlorine, using, as a radical initiator, decachlorobutane or an octachlorobutane such as octachlorobut-1-ene or a mixture containing these two products.

Good degrees of conversion and good yields are obtained at moderate temperatures.

The process is, for example, applicable to the substitution chlorination of benzene and of chloroform.

7 Claims, No Drawings

PROCESS FOR CARRYING OUT SUBSTITUTION CHLORINATION REACTIONS OF ORGANIC COMPOUNDS BY MEANS OF MOLECULAR CHLORINE IN THE PRESENCE OF A CHLORINATED PRODUCT SERVING AS A RADICAL INITIATOR, AND RADICAL INITIATORS USED IN SUCH A PROCESS

The present invention relates to a process for carrying out substitution chlorination reactions of organic compounds by means of molecular chlorine in the presence of a chlorinated product serving as a radical initiator. It also embraces the initiators to be used in such a process.

It is known that the substitution chlorination reactions of organic compounds frequently take place in accordance with a radical mechanism which can be initiated by the formation of chlorine atoms. This being the case, such substitution chlorination reactions are advantageously carried out under conditions which are able to favour the formation of atomic chlorine, especially by employing molecular chlorine at temperatures above 250° C. and/or in the presence of suitable catalysts or initiators or under the influence of actinic rays, or in the absence of molecular chlorine but employing specific chlorination agents such as hexachloroethane (at 430°–550° C.), carbon tetrachloride (at about 500° C.) or hexachlorocyclopentadiene (at 345° C.) (cf. W. DORREPAAL and R. LOUW-Int. J. Chem. Kinetics, 1978, 10, p. 249–275).

The known processes suffer from various disadvantages:

Photochlorination, though it permits working at low temperatures, leads to the formation of tarry by-products which foul the light tubes and give rise to a consequent reduction in the initiation radiation and hence in the reaction yield. Furthermore, these processes require working in reactors which are permeable to the initiation radiation, that is to say most commonly in glass, which makes it impossible to employ reactions carried out at high pressures.

The thermal processes result in substantial formation of tars, with consequent blockages of the reactor or of the pipelines, thereby preventing continuous operation of the process and causing considerable corrosion of the apparatus.

It is the object of the present invention to overcome these disadvantages while making it possible to make use of a byproduct which is troublesome in certain manufacturing processes of organic chlorinated products. In fact, the invention proposes carrying out the substitution chlorination of organic compounds by means of molecular chlorine in the presence of a small amount of a novel initiator which makes it possible to work at moderate temperatures and nevertheless to obtain an excellent degree of chlorination; the said initiator consists of a chlorinated derivative of hexachlorobuta-1,3-diene which, as is known, constitutes a toxic byproduct for which there are virtually no markets and which hitherto has had to be destroyed by burning.

The invention relates to a process for carrying out substitution chlorination reactions of organic compounds by means of molecular chlorine in the presence of a chlorinated product serving as a radial initiator, in which the radical initiator used is decachlorobutane or an octachlorobutene such as octachlorobut-1-ene or a mixture containing these chlorinated products. Preferably, the radical initiator used in this process results from the addition chlorination of hexachlorobuta-1,3-diene.

Non-limiting examples of such substitution chlorination reactions comprise the chlorination of methane, of ethane or of their halogenated derivatives as well as, in general, the chlorination of any of the acyclic or cyclic hydrocarbon compounds or of their halogenated derivatives. The process of the invention is in particular applicable to aromatic compounds, which can be substitutively chlorinated either in the aromatic nucleus or in the side chain or in both these positions, depending on the working conditions chosen and of course depending on the nature of the organic compound.

The invention also relates to the initiators for the substitution chlorination of organic compounds, which initiators consist of a chlorinated product or a mixture of chlorinated products which results from the addition chlorination of hexachlorobuta-1,3-diene and which principally comprises decachlorobutane and/or an octachlorobutene, depending on the degree to which the addition chlorination has been taken.

The said chlorinated products obtained by addition chlorination of hexachlorobuta-1,3-diene can be prepared in a manner known per se, for example by photochlorination or by liquid phase chlorination catalysed by iron.

These chlorinations lead to the formation of crude mixtures which in addition to the principal products mentioned above contain a small amount of hexachloroethane and possibly of unconverted hexachlorobuta-1,3-diene, as well as a small proportion of other compounds.

Thus, by way of example, there is given below the composition, in g/kg, of crude mixtures resulting from the photochlorination of hexachlorobuta-1,3-diene:

|  | Mixture A | Mixture B |
|---|---|---|
| Octachlorobut-1-ene | 415 | — |
| Decachlorobutane | 303 | 812 |
| Hexachloroethane | 183 | 147 |
| Hexachlorobuta-1,3-diene | 77 | <0.5 |
| Other compounds, unidentified | 22 | 41 |

On the other hand, a crude mixture obtained by chlorination of hexchlorobuta-1,3-diene (1190 g of $C_4Cl_6$ and 652 g of $Cl_2$) in an autoclave at 125° C., under a pressure of 9 bars, in the presence of about 0.1% by weight of $FeCl_3$ (catalyst), the chlorination product having been washed with hydrochloric acid to remove the $FeCl_3$, had the following composition:

|  | Mixture C g/kg |
|---|---|
| Octachlorobut-1-ene | 200 |
| Decachlorobutane | 615 |
| Hexachloroethane | 128 |
| Hexachlorobuta-1,3-diene | 25 |
| Other compounds, unidentified | 32 |

The amount of initiator employed in the process of the invention is in general between 0.01 and 10 mole % of the total amount of the reactants and diluent used. In general, this amount is from 0.01 to 5 mole % and preferably 0.1 to 2 mole % of initiator, relative to the reactants employed, is used.

The molecular chlorine and the organic compound to be chlorinated are generally employed in molar ratios of between 0.1 and 20 moles of chlorine per mole of organic compound. This ratio depends in particular on the number of hydrogen atoms which it is desired to replace. Preferably this ratio varies between 0.2 and 2 moles and molar ratios of between 0.3 and 10 moles of chlorine per mole of organic compound are very particularly preferred.

The abovementioned chlorination initiators are suitable for gas phase or liquid phase reactions. They can be used at atmospheric pressure or at a higher pressure. The temperature of course depends on the nature of the compound to be chlorinated and on the other working conditions, but under all circumstances.

for a given degree of chlorination and a given residence time, the use of the initiators according to the invention makes it possible to reduce the temperature, leading to a reduction in the formation of coke, tars and undesirable byproducts, at a given temperature and a given residence time, a higher degree of chlorination can be achieved, and this may allow a saving of energy by reducing the amount of organic substrate to be recycled, at a given temperature and a given degree of chlorination, the residence time can be reduced, which amounts to increasing the productivity of the reactor.

It has also been found that in certain cases it can be desirable, in order to minimise the overheating of the reaction mixture, to carry out the chlorination reaction in the presence of additives which act as diluents but which are inert towards the reactants and initiators employed in the reaction. As additives there are preferably employed aliphatic chlorinated derivatives such as carbon tetrachloride, or inorganic products such as hydrogen chloride or nitrogen.

Preferably, the process is carried out with carbon tetrachloride.

In general, the halogenated organic additives are introduced into the reaction medium in an amount of 1 to 25 moles per mole of organic compound employed.

The process according to the invention can be carried out in any apparatus or any reactor in which the working conditions described above can be met. Good results have been obtained in the apparatus described in the examples which follow. However, it is possible to work in other types of apparatus depending on the type of reaction carried out, especially in order to improve the selectivity; thus, depending on the particular case, reactors such as tubular reactors, homogeneous cascade reactors and the like may be selected.

The examples which follow illustrate the invention without however imposing a limitation thereon.

EXAMPLE 1

In this example, the substitution chlorination of benzene, essentially to give monochlorobenzene and dichlorobenzenes, was carried out at 300° C. in the absence of an initiator (by way of comparison) and in the presence of an initiator, namely that prepared by chlorination of hexachlorobuta-1,3-diene in the presence of $FeCl_3$, the composition of which initiator has been given above (20% by weight of $C_4Cl_8$ and 61.5% by weight of $C_4Cl_{10}$) (Mixture C).

The gas phase chlorination of benzene was carried out at atmospheric pressure in a spherical continuous mixer reactor of about 1 $dm^3$ capacity, made of pyrex, and self-stirred by gas jets (Chem. Eng. Sci. 1973, 28, p 129–137), the reactants being introduced in the gaseous form by means of a four-nozzle injector located in the centre of the sphere.

The reactor is placed in a chamber inside which the air is heated electrically and is stirred by means of a turbine so as to maintain the desired reaction temperature. A mixture of benzene and $CCl_4$, the latter being used as an inert diluent, is supplied via a vertical tubular evaporator heated electrically and connected to the injector. The chlorine gas is injected into the bottom of the evaporator tube. The initiator, where such is used, is added in liquid form, as a concentrated solution in $CCl_4$. The chlorination products leave the reactor through a nozzle located diametrically opposite to the inlet, and are then condensed and treated with aqueous NaOH to neutralise the residual chlorine and the HCl formed; after the phases have settled out, the organic phase is separated from the aqueous phase and analysed by vapour phase chromatography. The conditions and results of the experiments are given in Table 1 below.

TABLE 1

| | CHLORINATION OF BENZENE | |
|---|---|---|
| | REFERENCE EXPERIMENT, WITHOUT INITIATOR | EXPERIMENT WITH INITIATOR (MIXTURE C) |
| CONDITIONS | | |
| temperature in the reactor °C. | 300 | 300 |
| temperature at the evaporator outlet ($C_6H_6$ + $CCl_4$ + $Cl_2$) °C. | 150 | 151 |
| introduction of initiator | nil | 38% by weight solution in $CCl_4$ |
| mean residence time (= volume of the reactor/volume flow rate of the reactants) s | 10 | 10 |
| molar ratio of the reactants | | |
| benzene mol/mol | 1 | 1 |
| $Cl_2$ mol/mol | 2.0 | 2.0 |
| $CCl_4$ (inert diluent) mol/mol | 3.0 | 3.0 |
| initiator (sum of its constituents) mol/mol | 0 | 0.06 |
| initiator content of the reaction mixture % mol | 0 | 1.0 |
| RESULTS | | |
| distribution of the chlorination products | | |
| benzene % mol | 91.9 | 15.4 |
| monochlorobenzene % mol | 7.9 | 36.6 |
| dichlorobenzenes % mol | 0.2 | 37.9* |
| trichlorobenzenes % mol | 0 | 9.4 |

TABLE 1-continued

| CHLORINATION OF BENZENE | | |
|---|---|---|
| | REFERENCE EXPERIMENT, WITHOUT INITIATOR | EXPERIMENT WITH INITIATOR (MIXTURE C) |
| tetrachlorobenzenes % mol | 0 | 0.7 |
| conversion of benzene % | 8 | 85 |
| degree of chlorination (= moles of $Cl_2$ reacted/mole of benzene employed) mol/mol | 0.08 | 1.4 |

*Ortho/meta/para ratio = 11/64/25

It will be seen from these results that the addition of 1.0 mole % of initiator according to the invention, relative to the total amount of the substances participating in the reaction ($C_6H_6+Cl_2+CCl_4$) makes it possible:

to increase the conversion of benzene from 8 to 85% and to increase the degree of chlorination from 0.08 to 1.4 mole/mole.

Without initiator, monochlorobenzene is the principal chlorination product; in the presence of the initiator, a mixture of monochlorobenzene, dichlorobenzenes and trichlorobenzenes is formed.

EXAMPLE 2

Experiments on the chlorination of chloroform to give carbon tetrachloride were carried out at 220° and 250° C., under atmospheric pressure, in the installation of Example 1, in the absence and in the presence of the initiator according to the invention, and in the presence of hexachloroethane by way of comparison. The initiators, where used, are introduced in the form of a solution in $CHCl_3$. A deficiency of $Cl_2$ relative to the chloroform was used, the excess chloroform serving as a diluent. The conditions and results of the experiments are shown in Table 2. The initiator used is the same as that of Example 1.

At 220° C., the addition of 1.8 mole % of initiator according to the invention makes it possible to increase the ratio of $CCl_4$ formed/$Cl_2$ employed from about 0.02 or 0.03 to 0.52 mole/mole.

It will be noted that the addition of 1.8% by volume of hexachloroethane at 220° C. has no effect on the ratio of $CCl_4$ formed/$Cl_2$ employed.

At 250° C., this ratio increased from 0.09 mole/mole in the absence of initiator to 0.69 mole/mole when using 1.9 mole % of the chlorination product of hexachlorobuta-1,3-diene.

I claim:

1. Process for carrying out substitution chlorination reactions of organic compounds by means of molecular chlorine in the presence of a chlorinated product serving as a radical initiator, characterised in that the radical initiator used is decachlorobutane or an octachlorobutene such as octachlorobut-1-ene or a mixture containing these two products.

2. Process according to claim 1, characterised in that the radical initiator results from the addition chlorination of hexachlorobuta-1,3-diene.

3. Process according to claim 1, characterised in that the substitution chlorination is carried out at a temperature above 200° C.

TABLE 2

| | CHLORINATION OF CHLOROFORM | | | | |
|---|---|---|---|---|---|
| | (220° C.) REFERENCE EXPERIMENT WITHOUT INITIATOR | (220° C.) EXPERIMENT WITH INITIATOR (MIXTURE C) | (250° C.) REFERENCE EXPERIMENT WITHOUT INITIATOR | (250° C.) EXPERIMENT WITH INITIATOR (MIXTURE C) | (220° C.) REFERENCE EXPERIMENT WITH HEXA-CHLOROETHANE |
| CONDITIONS | | | | | |
| temperature in the reactor °C. | 220 | 220 | 250 | 250 | 220 |
| temperature at the evaporator outlet ($CHCl_3 + Cl_2$) °C. | 156 | 155 | 155 | 155 | 170 |
| mean residence time s | 10 | 10 | 10 | 10 | 10 |
| molar ratios of the reactants | | | | | |
| chloroform mol/mol | 1 | 1 | 1 | 1 | 1 |
| $Cl_2$ mol/mol | 0.33 | 0.34 | 0.33 | 0.33 | 0.33 |
| initiator (sum of its constituents) mol/mol | 0 | 0.025 | 0 | 0.026 | 0.024 |
| initiator content of the reaction mixture % mol | 0 | 1.8 | 0 | 1.9 | 1.8 |
| RESULTS | | | | | |
| distribution of the chlorination products | | | | | |
| chloroform % mol | 99.0 | 82.3 | 97.1 | 77.1 | 99.4 |
| carbon tetrachloride % mol | 1.0 | 17.7 | 2.9 | 22.9 | 0.6 |
| $CCl_4$ formed/$Cl_2$ employed mol/mol | 0.03 | 0.52 | 0.09 | 0.69 | 0.02 |

4. Process according to claim 1, characterised in that the amount of initiator employed is between 0.01 and 10 mole % of the total amount of the reactants and diluents employed.

5. Process according to claim 1, characterised in that the substitution chlorination is carried out at a pressure above atmospheric pressure.

6. Process according to claim 1, characterised in that it is applied to the substitution chlorination of benzene to give monochlorobenzene and dichlorobenzenes.

7. Process according to claim 1, characterised in that it is applied to the substitution chlorination of chloroform to give carbon tetrachloride.

* * * * *